US012674189B2

(12) United States Patent
White et al.

(10) Patent No.: US 12,674,189 B2
(45) Date of Patent: Jul. 7, 2026

(54) USE OF MICROBIAL CELL LINES TO MAXIMIZE ORGANIC ACID PRODUCTION

(71) Applicant: J&K Ingredients, LLC, Paterson, NJ (US)

(72) Inventors: Derrick White, Lincoln, NE (US); James S. Brophy, St. Louis Park, MN (US); Krishnamoorthy Pitchai, St. Louis Park, MN (US)

(73) Assignee: J&K Ingredients, LLC, Paterson, NJ (US)

( * ) Notice: Subject to any disclaimer, the term of this patent is extended or adjusted under 35 U.S.C. 154(b) by 744 days.

(21) Appl. No.: 17/799,622

(22) PCT Filed: Feb. 12, 2021

(86) PCT No.: PCT/US2021/017940
§ 371 (c)(1),
(2) Date: Aug. 12, 2022

(87) PCT Pub. No.: WO2021/163548
PCT Pub. Date: Aug. 19, 2021

(65) Prior Publication Data
US 2023/0097164 A1    Mar. 30, 2023

Related U.S. Application Data

(60) Provisional application No. 62/977,087, filed on Feb. 14, 2020.

(51) Int. Cl.
*C12P 39/00*    (2006.01)
*C12N 1/20*    (2026.01)
(Continued)

(52) U.S. Cl.
CPC ................ *C12P 39/00* (2013.01); *C12N 1/20* (2013.01); *C12P 7/46* (2013.01); *C12P 7/54* (2013.01); *C12P 7/56* (2013.01)

(58) Field of Classification Search
CPC .... C12P 39/00; C12P 7/46; C12P 7/54; C12P 7/56; C12P 7/52; C12N 1/20
See application file for complete search history.

(56) References Cited

U.S. PATENT DOCUMENTS

| | | | |
|---|---|---|---|
| 1,932,755 | A | 10/1933 | Stiles et al. |
| 10,808,266 | B2 | 10/2020 | Blum et al. |

(Continued)

FOREIGN PATENT DOCUMENTS

| | | |
|---|---|---|
| CN | 101967498 | 2/2011 |
| CN | 102076863 | 5/2011 |

(Continued)

OTHER PUBLICATIONS

Chaia et al., Short-chain fatty acids modulate growth of lactobacilli in mixed culture fermentations with propionibacteria, International Journal of Food Microbiology, vol. 26, Issue 3, 1995, pp. 365-374 (Year: 1995).*

(Continued)

*Primary Examiner* — Robert B Mondesi
*Assistant Examiner* — Naghmeh Nina Moazzami
(74) *Attorney, Agent, or Firm* — Fish & Richardson P.C.

(57)    ABSTRACT

Described herein are methods, microbial cell lines, and media used in co-culture to augment propionic acid production using an optimized fermentation medium and methods for increasing propionic acid yield, e.g., by co-culturing *Lacticbacillus Casei* and high-acid tolerant *A. Acidipropionici*.

20 Claims, 3 Drawing Sheets

(51) Int. Cl.

| | | |
|---|---|---|
| *C12P 7/46* | (2006.01) |
| *C12P 7/54* | (2006.01) |
| *C12P 7/56* | (2006.01) |

(56) References Cited

U.S. PATENT DOCUMENTS

| | | | |
|---|---|---|---|
| 11,613,769 | B2 | 3/2023 | Blum et al. |
| 12,054,763 | B2 | 8/2024 | Blum et al. |
| 2004/0033289 | A1 | 2/2004 | Selmer-Olsen |
| 2011/0151529 | A1 | 6/2011 | Yang |
| 2015/0275242 | A1 | 10/2015 | Osterhout et al. |
| 2017/0145467 | A1 | 5/2017 | Svagelj et al. |
| 2019/0382809 | A1 | 12/2019 | Blum |
| 2021/0040513 | A1 | 2/2021 | Blum |
| 2023/0265467 | A1 | 8/2023 | Blum et al. |
| 2024/0327879 | A1 | 10/2024 | Blum et al. |

FOREIGN PATENT DOCUMENTS

| | | | |
|---|---|---|---|
| CN | 102686718 | 9/2012 | |
| CN | 106868062 | 6/2017 | |
| CN | 107937314 | 4/2018 | |
| CN | 113614221 | 11/2021 | |
| EP | 0141642 | 5/1985 | |
| EP | 2648530 | 10/2013 | |
| FR | 2686897 | 8/1993 | |
| JP | S61-501885 A | 9/1986 | |
| JP | H08-066178 A | 3/1996 | |
| JP | 2008259451 | 10/2008 | |
| JP | 2011524749 | 10/2017 | |
| WO | WO 198504901 | 11/1985 | |
| WO | WO-2010078670 A2 * | 7/2010 | .......... A23L 1/3014 |
| WO | WO 2010097362 | 9/2010 | |
| WO | WO 2012064883 | 5/2012 | |
| WO | WO 2014099707 | 6/2014 | |
| WO | WO 2017055932 | 4/2017 | |
| WO | WO 2017185018 | 10/2017 | |
| WO | WO 2019245985 | 12/2019 | |

OTHER PUBLICATIONS

Fritze et al. Spore-forming, lactic acid producing bacteria of the genera *Bacillus* and *Sporolactobacillus*. In The genera of lactic acid bacteria (pp. 368-391). 1995. Boston, MA: Springer US (Year: 1995).*

Sabra et al., Substrate-limited co-culture for efficient production of propionic acid from flour hydrolysate, Appl Microbiol Biotechnol (2013) 97:5771â5777 (Year: 2013).*

Ngome et al. , Inoculum concentration and inoculation time for propionic acid production from whey using mixed culture of Lactobacillus helveticus and Propionibacterium freudenreichii PS-1. Acta Scientiarum. Technology, 2017, 39(05), 543-550 (Year: 2017).*

Office Action in Chinese Application No. 201980051169.0, dated Feb. 20, 2024, 18 pages (with English Translation).

European Extended Search Report in European Application No. EP 21753482, dated Jul. 18, 2023, 8 pages.

Taniguchi et al. "Production of a Mixture of Antimicrobial Organic Acids from Lactose by Co-Culture of *Bifidobacterium longum* and *Propionibacterium freudenreichii*," Biosci. Biotechnol. Biochem., Jan. 1998, 62(8):1522-1527.

Office Action in Mexican Appln. No. MX/a/2020/013848, mailed Jul. 9, 2024, 23 pages (with English Translation).

Abdel-Rahman et al., "Recent Advances in Lactic Acid Production by Microbial Fermentation Processes," Biotechnology Advances, Nov. 2013, 31(6):877-902.

Accession No. A0A0F3WHB9, Jun. 24, 2015, 5 pages.

Accession No. Q6AA87, Sep. 13, 2004, 2 pages.

Ahmadi et al., "An overview of biotechnological production of propionic acid: From upstream to downstream processes," Electronic Journal of Biotechnology, 2017, 28:67-75.

Border et al., "Production of Propionic Acid by Mixed Bacterial Fermentation," Biotechnology Letters, 1987, 9(12):843-848.

Coral, "Propionic acid production by *Propionibacterium* sp. using low-cost carbon sources in submerged fermentation," Dissertation, Federal University of Parana, 2008, 39 pages.

Duarte et al., "Microbial production of Propionic and Succinic acid from Sorbitol using *Propionibacterium acidipropionici*," AMB Express, 2015, 5(13):1-8.

Eitman and Ramalingam, "Microbial Production of Lactic Acid," Biotechnol. Lett., May 2015, 37(5): 955-75.

European Extended Search Report in EP Appln. No. 19823109.4, dated Feb. 14, 2022, 16 pages.

Gonzalez-Garcia et al., "Microbial Propionic Acid Production," Fermentation, 2017, 3:21, 20 pages.

Guan et al., "Comparative Genomics and Transcriptomics Analysis-Guided Metabolic Engineering of *Propionibacterium acidipropionici* for Improved Propionic Acid Production", Biotechnology and Bioengineering, Dec. 2017, 115(2):483-494.

Guan et al., "Metabolic engineering of acid resistance elements to improve acid resistance and propionic acid production of *Propionibacterium jensenii*," Biotechnology and Bioengineering, 2016, 113:1294-304.

Guan et al., "Understanding of how *Propionibacterium acidipropionici* respond to propionic acid stress at the level of proteomics," Scientific Reports, 2014, 4:6951.

Guan et al.," Genome-shuffling improves acid tolerance of Propionibacterium acidipropionici and propionic acid production," Advances in Chemistry Research, 2012, 15:143-152.

International Preliminary Report on Patentability in International Appln. No. PCT/US2019/037520, mailed on Dec. 22, 2020, 10 pages.

International Preliminary Report on Patentability, International Application No. PCT/US2021/019940, mailed on Aug. 25, 2022, 7 pages.

International Search Report and Written Opinion in International Application No. PCT/US2021/019940, mailed on May 3, 2021, 9 pages.

International Search Report and Written Opinion in International Application No. PCT/US2019/37520, mailed on Oct. 29, 2019, 17 pages.

Invitation to Pay Additional Fees in International Application No. PCT/US2019/37520, mailed on Aug. 30, 2019, 2 pages.

Jiang et al., "Enhanced propionic acid production from whey lactose with immobilized *Propionibacterium acidipropionici* and the role of trehalose synthesis in acid tolerance," Green Chem., 2015, 17:250-259.

Kagliwal et al., "Wheat flour based propionic acid fermentation: An economic approach, " Bioresource Technology, 2013, 139:694-699.

Kizer et al., "Application of Functional Genomics to Pathway Optimization for Increased Isoprenoid Production," Applied and Environmental Microbiology, May 2008, 74(10):3229-3241.

Liu et al., "Glycerol/Glucose Co-Fermentation: One More Proficient Process to Produce Propionic Acid by *Propionibacterium acidipropionici*," Curr Microbiol., 2011, 62:152-158.

Luna-Flores et al., "Improved production of propionic acid using genome shuffling," Biotechnology Journal, 2017, 12(2):1600120, 1-12.

Parizzi et al., "The genome sequence of *Propionibacterium acidipropionici* provides insights into its biotechnological and industrial potential", BMC Genomics, Oct. 2012, 13(562): 1-20.

Prather et al., "De novo biosynthetic pathways: rational design of microbial chemical factories," Current Opinion in Biotechnology, Oct. 2008, 19(5):468-474.

Rehberger et al., "Response of cultures of *Propionibacterium* to acid and low pH: tolerance and inhibition," Journal of Food Production, 1998, 61:211-216.

Scholz et al., "The natural history of cutaneous propionibacteria, and reclassification of selected species within the genus *Propionibacterium* to the proposed novel genera *Acidipropionibacterium* gen. nov., *Cutibacterium* gen. nov. and *Pseudopropionibacterium* gen. nov.," International Journal of Systematic and Evolutionary Microbiology, 2016, 66:4422-4432.

(56) References Cited

OTHER PUBLICATIONS

Stowers et al., "Development of an industrializable fermentation process for propionic acid production," J Ind. Microbiol. Biotechnol., 2014, 41:837-852.

Suwannakham et al., "Construction and characterization of *ack* knock-out mutants of *Propionibacterium acidipropionici* for enhanced propionic acid fermentation," Biotechnology and Bioengineering, 2006, 94:383-95.

Suwannakham et al., "Enhanced propionic acid fermentation by *Propionibacterium acidipropionici* mutant obtained by adaptation in a fibrous-bed bioreactor," Biotechnology and Bioengineering, 2005, 91:325-337.

Suwannakham, "Metabolic engineering for enhanced propionic acid fermentation by *Propionibacterium acidipropionici*," Dissertation, Ohio State University, 2005, 278 pages.

Thierry et al., "New insights into physiology and metabolism of *Propionibacterium freudenreichii*," International Journal of Food Microbiology, 2011, 149:19-27.

Tufvesson et al., "Economic and environmental assessment of propionic acid production by fermentation using different renewable raw materials," Bioresource Technology, 2013, 149:556-564.

Wang et al., "Engineering *Propionibacterium freudenreichii* subsp. *shermanii* for enhanced propionic acid fermentation: Effects of overexpressing propionyl-CoA:Succinate CoA transferase," Metabolic Engineering, 2015, 27:46-56.

Wang et al., "High Cell Density Propionic Acid Fermentation with an Acid Tolerant Strain of *Propionibacterium acidipropionici*," Biotechnology and Bioengineering, Mar. 2015, 112(3):502-511.

Wang et al., "Metabolic engineering of *Propionibacterium freudenreichii* subsp. *shermanii* for enhanced propionic acid fermentation: Effects of overexpressing three biotin-dependent carboxylases," Process Biochemistry, 2015, 50:194-204.

Wang et al., "Propionic acid production in glycerol/glucose co-fermentation by *Propionibacterium freudenreichii* subsp. *shermanii*," Biosource Technology, 2013, 137:116-123.

White, "Wheat Flour Hydrolysis Protocol," dated Mar. 5, 2018, 1 page.

Woskow et al., "Propionic acid production by a propionic acid-tolerant strain of *Propionibacterium acidipropionici* in batch and semicontinuous fermentation," Applied and Environmental Microbiology, 1991, 57(10):2821-2828.

Zhang et al., "Effects of carbon dioxide on cell growth and propionic acid production from glycerol and glucose by *Propionibacterium acidipropionici*," Bioresource Technology, 2015, 175:374-381.

Zhang et al., "Propionic acid production from glycerol by metabolically engineered *Propionibacterium acidipropionici*," Process Biochemistry, 2009, 44:1346-1351.

Zhu et al., "Optimization and scale-up of propionic acid production by propionic acid-tolerant *Propionibacterium acidipropionici* with glycerol as the carbon source," Bioresource Technology, 2010, 101:8902-8906.

Zhuge et al., "Improved propionic acid production from glycerol with metabolically engineered *Propionibacterium jensenii* by integrating fed-batch culture with a pH-shift control strategy," Bioresource Technology, Jan. 2014, 152:519-525.

Zhuge et al., "Improved propionic acid production with metabolically engineered *Propionibacterium jensenii* by an oxidoreduction potential-shift control strategy," Bioresource Technology, Jan. 2015, 175:606-612.

Ahmadi et al., "FED-Batch Fermentation For Propionic Acetic and Lactic Acid Production," Oriental Journal of Chemistry, Mar. 28, 2015, 31(1):581-590.

Office Action in Japanese Appln. No. 2022-549158, mailed on Mar. 28, 2025, 17 pages (with English Translation).

\* cited by examiner

USE OF MICROBIAL CELL LINES TO MAXIMIZE ORGANIC ACID PRODUCTION

CLAIM OF PRIORITY

This application is a national phase application of PCT Application No. PCT/US2021/017940, internationally filed Feb. 12, 2021, which claims the benefit of U.S. Provisional Application Ser. No. 62/977,087, filed on Feb. 14, 2020. The entire contents of the foregoing are incorporated herein by reference.

TECHNICAL FIELD OF THE INVENTION

The disclosure generally relates to methods, microbial cell lines and media used in co-culture to augment propionic acid production using an optimized fermentation medium as well as methods for increasing propionic acid yield, e.g., by co-culturing *Lactobacillus Casei* and high-acid tolerant *Acidipropionibacterium Acidipropionici*.

BACKGROUND

Organic acids are carbon-containing compounds having acidic properties. Examples of organic acids include acetic acid, citric acid, gluconic acid, lactic acid, and propionic acid, among many others. Since they are fully degradable, organic acids can be used in the production of biodegradable polymers. They also have other important industrial applications, including as food and feed additives, mainly as preservatives.

Propionic acid (PA) is a carboxylic acid that has gained significant commercial value and can be produced by microbial fermentation of sugars from several carbon sources (see, e.g., Gonzalez-Garcia et al., 2017 and Ahmadi et al., 2017). Propionic acid has historically been produced commercially using a "petrochemical" process because it was deemed economically feasible. This has changed as the cost of crude oil and petrochemicals have increased over the years, as has consumer demand for a natural source of propionic acid for use in foods, resulting in increased interest in production methods using microbial fermentation.

SUMMARY

In light of concerns about the use of non-renewable base products and their environmental impact, microbial biosynthesis of propionic acid using renewable energy sources on a commercial scale has gained significant interest. Described herein are methods for production of high-yield propionic acid in microbial fermentation medium containing glucose as a carbon source. These methods can be applied to commercial scale production of propionic acid.

The disclosure provides microbial cell lines suitable for industrial-scale production of organic acid by using co-culture and methods of maximizing organic acid yield using optimizing medium.

Thus, provided herein are methods for producing an organic acid. The methods can include culturing (i) acid-tolerant organic acid excreting microbes and (ii) acid-tolerant lactic acid producing microbes under controlled fermentative conditions in medium, wherein the pH of the medium is between about 5.8 and 6.5, to produce a higher yield of the organic acid as compared to a single microbial cell line being used under the same conditions.

In some embodiments, the acid-tolerant organic acid excreting microbes are *Propionibacterium, Anaerovibrio,*

*Bacteroides, Clostridium, Fusobacterium, Megasphaera, Propionispira, Selenomonas,* or *Veillonella* genus organisms. In some embodiments, the *Propionibacterium* genus organisms are *Acidipropionibacterium acidpropionii* (NFS 2018).

In some embodiments, the lactic acid producing microbes are cultured or spore-forming lactic acid producing organisms. In some embodiments, the non-sporulating and acid-tolerant lactic acid bacteria comprise *Lactococcus, Pediococcus, Oenococus, Enterococcus, Leuconostoc,* and *Bifidobacterium.* In some embodiments, the sporulating and acid-tolerant lactic acid bacteria comprise *Bacillus, Lactobacillus, Clostridum, Paenibacillus,* or Sporolactobacillus genus organisms. In some embodiments, the *Lactobacillus* genus organisms are *Lactobacillus casei,*

In some embodiments, the pH of the medium is about 6.0.

In some embodiments, the method comprises providing a starting media comprising glucose, yeast extract, $MgSO_4$, $NaPO_4$, Vitamin B12, and $KPO_4$, wherein the starting media has a pH about 6; adding the acid-tolerant organic acid excreting microbes to the media, and adding the lactic acid producing microbes to the media 6-36 hours later, e.g., 12-24 hours later; and maintaining the culture for a sufficient time to produce a desired amount of the organic acid.

In some embodiments, the lactic acid producing microbes provide carbon for the acid-tolerant organic acid excreting microbes. In some embodiments, the acid-tolerant organic acid excreting microbes consume glucose from whey (by-product of cheese production), grain (wheat, corn, or starch) or plant (beans) originating carbon sources and/or the lactic acid produced by one or more of the cultured or spore forming lactic acid producing organisms.

In some embodiments, the organic acids comprise Propionic acid; Acetic acid; Lactic acid; and/or Succinic acid.

In some embodiments, the controlled fermentative conditions comprise aerobic, anaerobic or both during the fermentation process.

Also provided herein is a method for producing an organic acid comprising providing acid-tolerant organic acid excreting microbe(s); providing acid-tolerant lactic acid producing microbe(s); providing a growth medium comprising a glucose carbon source and a lactose carbon source, and having a pH of between about 5.8 and about 6.5; adding the acid-tolerant organic acid excreting microbe(s) and the acid-tolerant lactic acid producing microbe(s) to the growth medium, thereby producing a culture; and incubating the culture under controlled fermentative conditions, thereby producing an organic acid.

In some embodiments, the acid-tolerant organic acid excreting microbe(s) is selected from the group consisting of *Propionibacterium, Anaerovibrio, Bacteroides, Clostridium, Fusobacterium, Megasphaera, Propionispira, Selenomonas, Veillonella,* and combinations thereof. In some embodiments the *Propionibacterium* genus microbe(s) is *Acidipropionibacterium acidpropionii* (NFS 2018).

In some embodiments, the acid-tolerant organic acid excreting microbe(s) is provided as a growing culture.

In some embodiments, the acid-tolerant lactic acid producing microbe(s) is selected from the group consisting of *Lactococcus, Pediococcus, Oenococus, Enterococcus, Leuconostoc, Bifidobacterium, Bacillus, Lactobacillus, Clostridum, Paenibacillus,* Sporolactobacillus, and combinations thereof.

In some embodiments, the acid-tolerant lactic acid producing microbe(s) is selected from the group consisting of *Lactococcus, Pediococcus, Oenococus, Enterococcus, Leuconostoc, Bifidobacterium, Bacillus.*

In some embodiments, the acid-tolerant lactic acid producing microbe(s) is provided as a growing culture.

In some embodiments, the acid-tolerant lactic acid producing microbe(s) is selected from the group consisting of *Bacillus, Lactobacillus, Clostridum, Paenibacillus*, Sporolactobacillus, and combinations thereof. In some embodiments, the acid-tolerant lactic acid producing microbe(s) is *Lactobacillus casei*.

In some embodiments, the acid-tolerant lactic acid producing microbe(s) is provided as a spore, optionally wherein the spore is provided as part of the carbon source.

In some embodiments, the pH of the medium is about 6.0.

In some embodiments, the growth medium further comprises a nitrogen source, vitamin(s), $MgSO_4$, $NaPO_4$, and $KPO_4$.

In some embodiments, the glucose carbon source and the lactose carbon source are the same. In some embodiments, the glucose carbon source and the lactose carbon source are different.

In some embodiments, the glucose carbon source is a plant-based glucose carbon source. In some embodiments, the plant carbon source is selected from the group consisting of hydrolyzed wheat, hydrolyzed corn, hydrolyzed beans, hydrolyzed starch, and combinations thereof.

In some embodiments, the lactose carbon source is whey.

In some embodiments, the nitrogen source is selected from yeast extract, peptides, ammonia sulfate, ammonia hydroxide, amino acids, and combinations thereof. In some embodiments, the nitrogen source is yeast extract.

In some embodiments, the vitamin is vitamin B12.

In some embodiments, the acid-tolerant lactic acid producing microbe(s) are added to the media 6-36 hours, optionally 12-24 hours, after the acid-tolerant organic acid excreting microbe(s) are added to the media; and maintaining the culture for a time sufficient to produce a desired amount of the organic acid.

In some embodiments, the organic acids is selected from the group consisting of propionic acid, acetic acid, lactic acid, succinic acid, and combinations thereof.

The words "glucose" and "dextrose" are used interchangeably herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF INVENTION

Figure 1:
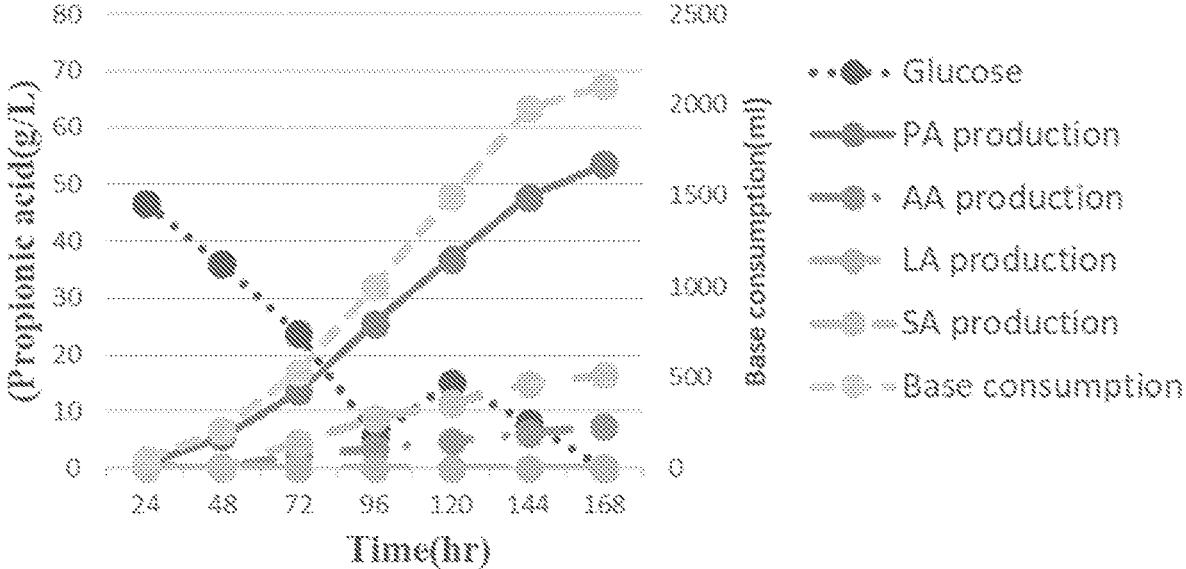
FIG. 1 shows organic acid production by *A. acidopropionici* (NFS-2018) in a bioreactor using fermented sugar medium using 5% inoculum in a 30 L working volume, temperature maintained at 30° C., and pH 6 (NaOH as neutralizing base).
Figure 2:
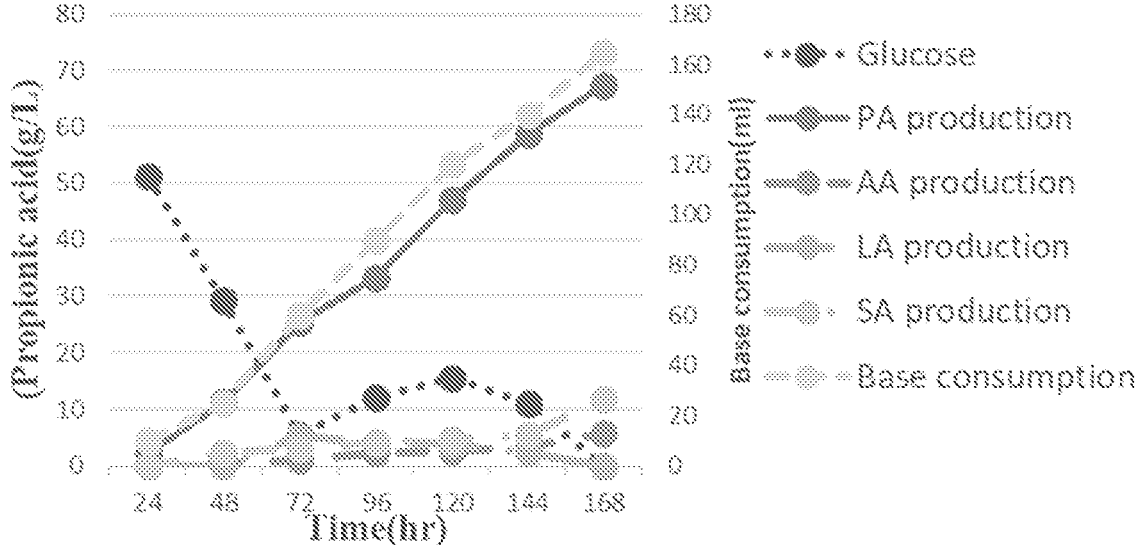
FIG. 2 shows organic acid production by *A. acidopropionici* (NFS-2018) and *Lactobacillus casei* in a bioreactor using fermented sugar medium using 5% inoculum in a 1 L working volume, temperature maintained at 30° C., and pH 6 (NaOH, neutralizing base).
Figure 3:
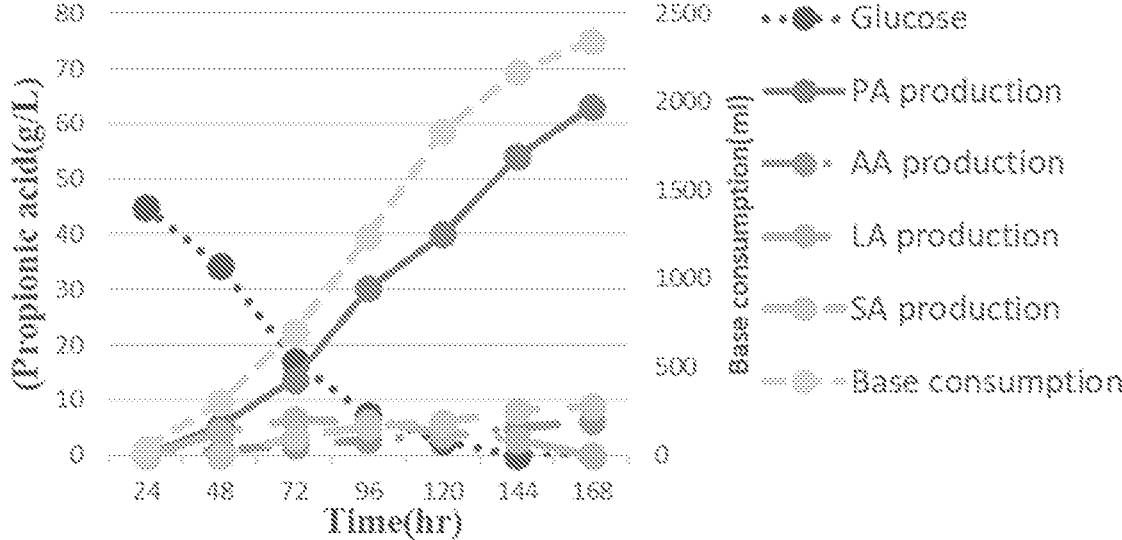
FIG. 3 shows organic acid production by *A. acidopropionici* (NFS-2018) and *Lactobacillus casei* in a bioreactor using fermented sugar medium using 5% inoculum in a 30 L working volume, temperature maintain at 30° C., and pH 6 (NaOH, neutralizing base).

Propionic acid (PA) is used as anti-mycotic agent to control the growth of yeast and mold in food products in applications such as bakery, dairy, meat, poultry, and pet foods. Propionic acid is also widely used as an intermediate in the production of various chemical end-products that are used in herbicides, perfumes, and other products.

Production of propionic acid is generally achieved through fermentation of carbon and nitrogen source-containing medium with a suitable microbial cell line. Typically, *Propionibacterium* genus organisms are used to convert carbon sources into propionic acid and other metabolites in the medium. *Propionibacterium* cell growth rate in fermentation medium is usually limited due to the inhibitory effects of propionic acid accumulation and availability of nutrients over the fermentation time. Methods have been developed to improve propionic acid production by developing acid-tolerant *Propionibacterium* strains and co-culturing the microorganisms. However, production yields were still limited due to an imbalance of nutrients for the microorganisms. Described herein are methods for fed-batching carbon sources and addition of *Lactobacillus casei* (co-fermentation) at an optimized time step to increase the production of propionic acid yield.

Although other bacteria can make propionic acid, *Propionibacterium* is the most commonly used bacteria that excretes propionic acid and has been studied extensively (Gonzalez-Garcia et al., 2017). Advancements in medium formulation, strain developments, and optimization of fermentation parameters have led to propionic acid production yields ranging from 25 to 50 g/l of propionic acid in the broth (media) (Gonzalez-Garcia et al., 2017, Stower et al., 2014, Wang et al., 2014, 2014 Liu et al., 2011, Kagliwal et al., 2013). There have also been reports of propionic acid production reaching 100+g/L during fermentation; however these values were generated by extending the fermentation for weeks to months making it not feasible for commercial scale up (Zhang and Yang, 2009, Wang et al., 2014 and Jiang et al., 2015).

Not only have there been improvements using the strategies described above, but there have also been efforts to increase propionic acid productivity by using mixed cultures. For example, co-culture methods have been used to produce PA using whey as feedstock (WO 85/04901; EP 0141642 A1). WO 85/04901 describes the use of *Lactobacillus casei* subspecies *rhamnosus* in the presence of *Veillonella criceti* to convert lactate to propionate via a two-stage fermentation process. In the first stage, carbohydrates are converted to lactic acid by *L. casei*; in the second stage, lactic acid is fermented to PA by *V. criceti*. (The genera *Lactobacillus* and *Veillonella* both belong to the phylum Firmicutes, whereas the genus *Propionibacterium* belongs to the phylum Actinobacteria.) EP 0141642 also describes the use of a mixed culture of lactic acid-producing bacteria (*L. casei*) and PA-producing bacteria (*P. shermanii*) to maximize the fermentation yield. The co-culture systems of WO 85/04901 and EP 0141642 are reported to be very productive in terms of PA production from lactose, with final yields ranging from 20-100 g/L. However, such co-culture systems have considerable implications for process parameters. For example, they suffer from a lack of control over the growth and metabolic activity of each organism in the system, which can lead to failure of either organism to grow or to contribute to formation of the desired product. A lack of reproducibility is common with co-culture systems. A study by Border et al, 1987 showed an increase of propionic acid production from 20 g/L to 30 g/l when a *Lactobacillus* strain was added to the fermentation. Other process using the mixed culture showed an increase up to 65 g/L of propionic acid in the broth when using mixed cultures however this process was done exclusively using whey (EP0141642 A1).

In the present disclosure, a process has been developed to maximize propionic acid production using a simplified medium, using glucose from multiple carbon sources such as wheat flour and starch while producing other organic acids during this process. This process can be used for all propionic acid and lactic acid producing bacteria and fermentation can be conducted with and without the addition of nitrogen gas to make the medium anaerobic during the mixed culture fermentation. As shown herein, when propionic acid bacteria (e.g., NFS-2018) was fermented with glucose without the addition of lactic acid bacteria, the propionic acid yield was around 5.3% within 168 hrs. Upon the addition of lactic acid bacteria to the fermenter, propionic acid production was boosted by 1.4% with a final yield of 6.7% propionic acid using the co-culture method.

Described herein are methods using co-culture of microbial cell lines to increase organic acid production. The methods use a microbial cell line that produces organic acids (e.g., *Acidipropionibacterium*) in a pH-controlled medium supplemented with a carbon source for 24 hrs with the addition of another microbial cell line (e.g., *Lactobacillus*) to further enhance organic acid production. In some embodiments, throughout the fermentation, the bioreactor is maintained at a temperature of 30° C. In some embodiments, under these cultivation conditions pH is maintained at 6. In some embodiments, the microbial cell lines can be cultivated for the same duration of time for all fermenters and bioreactors. In some embodiments, the microbial cell lines were inoculated into the fermenters and bioreactors at the same time.

In some embodiments, propionic acid can be produced through co-culture of *Lactobacillus Casei* and high acid-tolerant *Acidipropionibacterium acidipropionici* NFS-2018. As shown herein, propionic acid yield was improved from 50 g/L in mono-culture to 65 g/L using the co-culture fermentation methods described herein. The *Lactobacillus casei* was added to the microbial fermentation at an optimized time step to maximize propionic acid yield. From the co-culture fermentation, besides propionic acid, fermented broth contained 7 to 8 g/L of acetic acid and 9 to 10 g/L of succinic acid as co-metabolites.

Organic Acid Excreting Microbes

The present methods include the use of an organic acid-producing bacteria, e.g., propionibacteria. *Propionibacterium* is the microorganism most often used in the production of PA (as well as vitamin B12 and Swiss cheese). *Propionibacterium* is a gram-positive, non-motile, non-spore forming, rod-shaped, anaerobic genus of bacteria that includes the species *P. freudenreichii, P. acidifaciens, P. cyclohexanicum, P. australiense, P. acidipropionici, P. jensenii, P. thoenii, P. microaerophilum, P. olivae, P. damnosum, P. propionicum, P. acnes, P. avidum, P. granulosum, P. humerusii,* and *P. lymphophilum.* For industrial PA production, the most commonly used strain is *P. acidipropionici.* (A proposal has been made to reclassify the species within the genus *Propionibacterium* into three novel genera: *Acidipropionibacterium, Cutibacterium,* and *Pseudopropionibacterium* (Scholz & Kilian 2016). However, *Propionibacterium acidipropionci* and *Acidipropionibacterium acidipropionici* are still used somewhat interchangeably. The optimal pH and temperature for *Propionibacterium* cell growth are about 6.0-7.0 and about 30-37° C., respectively (Ahmadi et al. 2017). Cell growth is inhibited in pH less than about 5.0, although fermenters started at neutral pH can reach pH 4.4 (Rehberger and Glatz 1998). Ahmadi et al. provides an overview of PA production on several carbon sources by various species of *Propionibacterium* as reported in the literature (Ahmadi et al. 2017) and is incorporated herein by reference.

PA can also be produced by other anaerobic bacteria, such as certain species of Anaerovibrio, *Bacteroides, Clostridium, Fusobacterium, Megasphaera, Propionispira, Selenomonas,* and *Veillonella.*

In preferred embodiments, the organic acid producing microbe is acid tolerant, e.g., able to grow and produced propionic acid between the pH of 5-7.5. In some embodiments, the acid producing microbe is the high acid-tolerant *Acidipropionibacterium acidipropionici* (NFS-2018) as described in WO 2019/245985, deposited at ATCC as PTA-125895. In some embodiments, the acid producing microbe is not *Acidipropionibacterium shermanii* (ATCC 39393) (see EP0141642 A1).

In some embodiments, the organic acid producing microbe is wild-type. In some embodiments, the organic acid producing microbe is engineered.

Lactic Acid Producing Microbes

The present methods include the use of a lactic acid-producing microbes, e.g., lactic acid producing bacteria (LAB). In some embodiments, the microbe is from the genus *Lactobacillus,* e.g., *Lactobacillus casei.*

In some embodiments, the lactic acid-producing microbe is selected from lactic acid bacteria (LAB), *Bacillus, E. coli, Corynebacterium glutamicum,* and combinations thereof. See, e.g., Abdel-Rahman et al., "Recent Advances in Lactic Acid Production by Microbial Fermentation Processes," *Biotechnology Advances* 31:877-902 (2013).

In some embodiments, the LAB is homofermentative. In some embodiments, the LAB is heterofermentative. See, e.g., Eitman and Ramalingam, "Microbial Production of Lactic Acid," *Biotechnol. Lett.* 37:955-72 (2015).

In some embodiments, the methods include the use of a mixture of LABs. In some embodiments, the mixture includes both homofermentative and heterofermentative LABs.

In some embodiments, the lactic acid producing microbe is wild-type. In some embodiments, the lactic acid producing microbe is engineered.

Carbon Sources

A number of carbon sources have been used for microbial PA production, including glucose, fructose, maltose, sucrose, xylose, lactose, glycerol, lactate, flour hydrolysate, molasses, whey, and combinations thereof.

In some embodiments, hydrolyzed wheat flour is used as the carbon source. Methods for hydrolyzing wheat flour are known in the art, and can include the use of enzymatic hydrolysis, e.g., as described in Kagliwal et al., 2013. In some embodiments, the enzymatic hydrolysis includes using bacterial alpha-amylase at 90° C./pH 6.0 and then glucoamylase and protease at 60° C./pH 7.0.

In some embodiments, corn or another starch is used as the carbon source.

In some embodiments, a dairy carbon source is used, e.g., whey from cheese production.

In some embodiments, a mixture of sources are used as the carbon source. In some embodiments, the mixture of carbon sources comprises a glucose carbon source and a lactose carbon source.

In some embodiments, the glucose carbon source is derived from a plant carbon source, e.g., hydrolyzed grain and/or beans.

In some embodiments, the lactose carbon source is derived from a dairy source, e.g., whey from cheese production.

Nitrogen Sources

A number of nitrogen sources have been used for microbial PA production. In some embodiments, the nitrogen sources is yeast extract. In some embodiments, the nitrogen source is selected from yeast extract, peptides, ammonia sulfate, ammonia hydroxide, amino acids, and combinations thereof.

Media and Growth Conditions

An exemplary simplified media for use in the present methods can include glucose, yeast extract, $MgSO_4$, $NaPO_4$, Vitamin B12, and $KPO_4$, wherein the starting media has a pH of about 6.

In some embodiments, the media has a pH of about 5.5 to about 6.9. In some embodiments, the media has a pH of about 5.5 to about 6.8, about 5.5. to about 6.7, about 5.5 to about 6.6, about 5.5 to about 6.5, about 5.5 to about 6.4, about 5.5 to about 6.3, about 5.5 to about 6.2, about 5.5 to about 6.1, about 5.5 to about 6.0, about 5.5 to about 5.9, about 5.5 to about 5.8, about 5.5 to about 5.7, about 5.5 to about 5.6, about 5.6 to about 6.9, 5.6 to about 6.8, about 5.6. to about 6.7, about 5.6 to about 6.6, about 5.6 to about 6.5, about 5.6 to about 6.4, about 5.6 to about 6.3, about 5.6 to about 6.2, about 5.6 to about 6.1, about 5.6 to about 6.0, about 5.6 to about 5.9, about 5.6 to about 5.8, about 5.6 to about 5.7, about 5.7 to about 6.9, 5.7 to about 6.8, about 5.7. to about 6.7, about 5.7 to about 6.6, about 5.7 to about 6.5, about 5.7 to about 6.4, about 5.7 to about 6.3, about 5.7 to about 6.2, about 5.7 to about 6.1, about 5.7 to about 6.0, about 5.7 to about 5.9, about 5.7 to about 5.8, about 5.8 to about 6.9, 5.8 to about 6.8, about 5.8. to about 6.7, about 5.8 to about 6.6, about 5.8 to about 6.5, about 5.8 to about 6.4, about 5.8 to about 6.3, about 5.8 to about 6.2, about 5.8 to about 6.1, about 5.8 to about 6.0, about 5.8 to about 5.9, about 5.9 to about 6.9, 5.9 to about 6.8, about 5.9. to about 6.7, about 5.9 to about 6.6, about 5.9 to about 6.5, about 5.9 to about 6.4, about 5.9 to about 6.3, about 5.9 to about 6.2, about 5.9 to about 6.1, about 5.9 to about 6.0, about 6.0 to about 6.9, 6.0 to about 6.8, about 6.0. to about 6.7, about 6.0 to about 6.6, about 6.0 to about 6.5, about 6.0 to about 6.4, about 6.0 to about 6.3, about 6.0 to about 6.2, about 6.0 to about 6.1, about 6.1 to about 6.9, 6.1 to about 6.8, about 6.1. to about 6.7, about 6.1 to about 6.6, about 6.1 to about 6.5, about 6.1 to about 6.4, about 6.1 to about 6.3, about 6.1 to about 6.2, about 6.2 to about 6.9, 6.2 to about 6.8, about 6.2. to about 6.7, about 6.2 to about 6.6, about 6.2 to about 6.5, about 6.2 to about 6.4, about 6.2 to about 6.3, about 6.3 to about 6.9, 6.3 to about 6.8, about 6.3. to about 6.7, about 6.3 to about 6.6, about 6.3 to about 6.5, about 6.3 to about 6.4, about 6.4 to about 6.9, 6.4 to about 6.8, about 6.4. to about 6.7, about 6.4 to about 6.6, about 6.4 to about 6.5, about 6.5 to about 6.9, 6.5 to about 6.8, about 6.5 to about 6.7, about 6.5 to about 6.6, 6.6 to about 6.9, 6.6 to about 6.8, about 6.6. to about 6.7, about 6.7 to about 6.9, 6.7 to about 6.8, or about 6.8 to about 6.9

In some embodiments, the media comprises from about 1 to about 10% w/v of a carbon source, e.g., glucose. In some embodiments, the media comprises from about 1 to about 10, about 1 to about 9.5, about 1 to about 9, about 1 to about 8.5, about 1 to about 8, about 1 to about 7.5, about 1 to about 7, about 1 to about 6.5, about 1 to about 6, about 1 to about 5.5, about 1 to about 5, about 1 to about 4.5, about 1 to about 4, about 1 to about 3.5, about 1 to about 3, about 1 to about 2.5, about 1 to about 2, about 1 to about 1.5, about 1.5 to about 10, about 1.5 to about 9.5, about 1.5 to about 9, about 1.5 to about 8.5, about 1.5 to about 8, about 1.5 to about 7.5, about 1.5 to about 7, about 1.5 to about 6.5, about 1.5 to about 6.0, about 1.5 to about 5.5, about 1.5 to about 5, about 1.5 to about 4.5, about 1.5 to about 4, about 1.5 to about 3.5, about 1.5 to about 3, about 1.5 to about 2.5, about 1.5 to about 2, about 2 to about 10, about 2 to about 9.5, about 2 to about 9, about 2 to about 8.5, about 2 to about 8, about 2 to about 7.5, about 2 to about 7, about 2 to about 6.5, about 2 to about 6, about 2 to about 5.5, about 2 to about 5, about 2 to about 4.5, about 2 to about 4, about 2 to about 3.5, about 2 to about 3, about 2 to about 2.5, about 2.5 to about 10, about 2.5 to about 9.5, about 2.5 to about 9, about 2.5 to about 8.5, about 2.5 to about 8, about 2.5 to about 7.5, about 2.5 to about 7, about 2.5 to about 6.5, about 2.5 to about 6, about 2.5 to about 5.5, about 2.5 to about 5, about 2.5 to about 4.5, about 2.5 to about 4, about 2.5 to about 3.5, about 2.5 to about 3, about 3 to about 10, about 3 to about 9.5, about 3 to about 9, about 3 to about 8.5, about 3 to about 8, about 3 to about 7.5, about 3 to about 7, about 3 to about 6.5, about 3 to about 6, about 3 to about 5.5., about 3 to about 5.0, about 3 to about 4.5, about 3 to about 4, about 3 to about 3.5, about 3.5 to about 10, about 3.5 to about 9.5, about 3.5 to about 9, about 2.5 to about 8.5, about 3.5 to about 8, about 3.5 to about 7.5, about 3.5 to about 7, about 3.5 to about 6.5, about 3.5 to about 6, about 3.5 to about 5.5, about 3.5 to about 5, about 3.5 to about 4.5, about 3.5 to about 4, about 4 to about 10, about 4 to about 9.5, about 4 to about 9, about 4 to about 8.5, about 4 to about 8, about 4 to about 7.5, about 4 to about 7, about 4 to about 6.5, about 4 to about 6, about 4 to about 5.5, about 4 to about 5, about 4 to about 4.5, about 4.5 to about 10, about 4.5 to about 9.5, about 4.5 to about 9, about 4.5 to about 8.5, about 4.5 to about 8, about 4.5 to about 7.5, about 4.5 to about 7, about 4.5 to about 6.5, about 4.5 to about 6, about 4.5 to about 5.5, about 4.5 to about 5, about 5 to about 10, about 5 to about 9.5, about 5 to about 9, about 5 to about 8.5, about 5 to about 8, about 5 to about 7.5, about 5 to about 7, about 5 to about 6.5, about 5 to about 6, about 5 to about 10, about 5 to about 9.5, about 5 to about 9, about 5 to about 8.5, about 5 to about 8, about 5 to about 7.5, about 5 to about 7, about 5 to about 6.5, about 5 to about 6, about 5 to about 5.5, about 5.5 to about 10, about 5.5 to about 9.5, about 5.5. to about 9, about 5.5 to about 8.5, about 5.5 to about 8, about 5.5 to about 7.5, about 5.5 to about 7, about 5.5 to about 6.5, about 5.5 to about 6, about 6 to about 10, about 6 to about 9.5, about 6 to about 9, about 6 to about 8.5, about 6 to about 8, about 6 to about 7.5, about 6 to about 7, about 6 to about 6.5, about 6.5 to about 10, about 6.5 to about 9.5, about 6.5 to about 9, about 6.5 to about 8.5, about 6.5 to about 8, about 6.5 to about 7.5, about 6.5 to about 7, about 7 to about 10, about 7 to about 9.5, about 7 to about 9, about 7 to about 8.5, about 7 to about 8, about 7 to about 7.5, about 7.5 to about 10, about 7.5 to about 9.5, about 7.5 to about 9, about 7.5 to about 8.5, about 7.5 to about 8, about 8 to about 10, about 8 to about 9.5, about 8 to about 9, about 8 to about 8.5, about 8.5 to about 10, about 8.5 to about 9.5, about 8.5 to about 9, about 9 to about 10, about 9 to about 9.5, or about 9.5 to about 10% w/v of a carbon source, e.g., glucose.

In some embodiments, the media comprises from about 1 to about 2.5% w/v of a nitrogen source, e.g., yeast extract. In some embodiments, the media comprises from about 1 to about 2.4, about 1 to about 2.3, about 1 to about 2.2, about 1 to about 2.1, about 1 to about 2, about 1 to about 1.9, about 1 to about 1.8, about 1 to about 1.7, about 1 to about 1.6, about 1 to about 1.5, about 1 to about 1.4, about 1 to about 1.3, about 1 to about 1.2, about 1 to about 1.1, about 1.1 to about 2.5, about 1.1 to about 2.4, about 1.1 to about 2.3, about 1.1 to about 2.2, about 1.1 to about 2.1, about 1.1 to about 2, about 1.1 to about 1.9, about 1.1 to about 1.8, about 1.1 to about 1.7, about 1.1 to about 1.6, about 1.1 to about 1.5, about 1.1 to about 1.4, about 1.1 to about 1.3, about 1.1 to about 1.2, about 1.2 to about 2.5, about 1.2 to about 2.4, about 1.2 to about 2.3, about 1.2 to about 2.2, about 1.2 to about 2, about 1.2 to about 1.9, about 1.2 to about 1.8, about 1.2 to about 1.7, about 1.2 to about 1.6, about 1.2 to about 1.5, about 1.2 to about 1.4, about 1.2 to about 1.3, about 1.3 to about 2.5, about 1.3 to about 2.4, about 1.3 to about 2.3, about 1.3 to about 2.2, about 1.3 to about 2.1, about 1.3 to about 2, about 1.3 to about 1.9, about 1.3 to about 1.8, about 1.3 to about 1.7, about 1.3 to about 1.6, about 1.3 to about 1.5, about 1.3 to about 1.4, about 1.4 to about 2.5, about 1.4 to about 2.4, about 1.4 to about 2.3, about 1.4 to about 2.2, about 1.4 to about 2.1, about 1.4 to about 2, about 1.4 to about 1.9, about 1.4 to about 1.8, about 1.4 to about 1.7, about 1.4 to about 1.6, about 1.4 to about 1.5, about 1.5 to about 2.5, about 1.5 to about 2.4, about 1.5 to about 2.3, about 1.5 to about 2.2, about 1.5 to about 2.1, about 1.5 to about 2, about 1.5 to about 1.9, about 1.5 to about 1.8, about 1.5 to about 1.7, about 1.5 to about 1.6, about 1.6 to about 2.5, about 1.6 to about 2.4, about 1.6 to about 2.3, about 1.6 to about 2.2, about 1.6 to about 2.1, about 1.6 to about 2, about 1.6 to about 1.9, about 1.6 to about 1.8, about 1.6 to about 1.7, about 1.7 to about 2.5, about 1.7 to about 2.4, about 1.7 to about 2.3, about 1.7 to about 2.2, about 1.7 to about 2.1, about 1.7 to about 2, about 1.7 to about 1.9, about 1.7 to about 1.8, about 1.8 to about 2.5, about 1.8 to about 2.4, about 1.8 to about 2.3, about 1.8 to about 2.2, about 1.8 to about 2.1, about 1.8 to about 2, about 1.8 to about 1.9, about 1.9 to about 2.5, about 1.9 to about 2.4, about 1.9 to about 2.3, about 1.9 to about 2.2, about 1.9 to about 2.1, about 1.9 to about 2, about 2 to about 2.5, about 2 to about 2.4, about 2 to about 2.3, about 2 to about 2.2, about 2 to about 2.1, about 2.1 to about 2.5, about 2.1 to about 2.4, about 2.1 to about 2.3, about 2.1 to about 2.2, about 2.2 to about 2.5, about 2.2 to about 2.4, about 2.2 to about 2.3, about 2.3 to about 2.5, about 2.3 to about 2.4, or about 2.4 to about 2.5% w/v of a nitrogen source, e.g., yeast extract. In some embodiments, the media comprises about 2% w/v of a nitrogen source, e.g., yeast extract.

In some embodiments, the media comprises from about 0.2 to about 0.8 g/L $MgSO_4$. In some embodiments, the media comprises from about 0.2 to about 0.7, about 0.2 to about 0.6, about 0.2 to about 0.5, about 0.2 to about 0.4, about 0.2 to about 0.3, about 0.3 to about 0.8, about 0.3 to about 0.7, about 0.3 to about 0.6, about 0.3 to about 0.5, about 0.3 to about 0.4, about 0.4 to about 0.8, about 0.4 to about 0.7, about 0.4 to about 0.6, about 0.4 to about 0.5, about 0.5 to about 0.8, about 0.5 to about 0.7, about 0.5 to about 0.6, about 0.6 to about 0.8, about 0.6 to about 0.7, or about 0.7 to about 0.8 g/L $MgSO_4$. In some embodiments, the media comprises about 0.4 g/L $MgSO_4$.

In some embodiments, the media comprises from about 0.5 to about 3.0 g/L $NaPO_4$. In some embodiments, the media comprises from about 0.5 to about 2.5, about 0.5 to about 2, about 0.5 to about 1.5, about 0.5 to about 1, about 1 to about 3, about 1 to about 2.5, about 1 to about 2, about 1 to about 1.5, about 1.5 to about 3, about 1.5 to about 2.5, about 1.5 to about 2, about 2 to about 2.5, or about 2.5 to about 3 g/L $NaPO_4$. In some embodiments, the media comprises about 1 g/L $NaPO_4$.

In some embodiments, the media comprises from about 0.0015 to about 0.004 g/L of a vitamin source, e.g., vitamin B12. In some embodiments, the media comprises from about 0.0020 to about 0.0040, about 0.0020 to about 0.0035, about 0.0020 to about 0.0030, about 0.0020 to about 0.0025, about 0.0025 to about 0.0040, about 0.0025 to about 0.0035, about 0.0025 to about 0.0030, about 0.0030 to about 0.0040, about 0.0030 to about 0.0035, or about 0.0035 to about 0.0040 g/L of a vitamin source, e.g., vitamin B12.

In some embodiments, the media comprises from about 0.5 to about 3.0 g/L $KPO_4$. In some embodiments, the media comprises from about 0.5 to about 2.5, about 0.5 to about 2, about 0.5 to about 1.5, about 0.5 to about 1, about 1 to about 3, about 1 to about 2.5, about 1 to about 2, about 1 to about 1.5, about 1.5 to about 3, about 1.5 to about 2.5, about 1.5 to about 2, about 2 to about 2.5, or about 2.5 to about 3 g/L $KPO_4$. In some embodiments, the media comprises about 1 g/L $KPO_4$.

Methods for preparing the media are known in the art and provided herein.

In some embodiments, the media in which the organisms are cultured does not include one or more, e.g., all of dipotassium hydrogen phosphate; potassium dihydrogen phosphate; ferrous sulfate; 5,6 diamenobenzimidazole; cobaltous chloride; Mangenese sulfate; Enzymes; Protease; or calcium carbonate.

In some embodiments, the media is inoculated with about 1 to about 10% v/v of a culture of an organic acid producing microbe, e.g., a propionic acid producing microbe, e.g., *Acidipropionibacterium acidipropionici* (*A. acidopropionici*), e.g., *A. acidopropionici* (NFS-2018). In some embodiments, the media is inoculated with about 1 to about 9, about 1 to about 8, about 1 to about 7, about 1 to about 6, about 1 to about 5, about 1 to about 4, about 1 to about 3, about 1 to about 2, about 2 to about 10, about 2 to about 9 about 2 to about 8, about 2 to about 7, about 2 to about 6, about 2 to about 5, about 2 to about 4, about 2 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 9 to about 10% v/v of a culture of an organic acid producing microbe, e.g., a propionic acid producing microbe, e.g., *A. acidopropionici*, e.g., *A. acidopropionici* (NFS-2018).

In some embodiments, the culture of an organic acid producing microbe, e.g., a propionic acid producing microbe, e.g., *A. acidopropionici*, e.g., *A. acidopropionici* (NFS-2018), comprises about 5 to about 7 OD/ml (optical density) of cells. In some embodiments, the culture of an organic acid producing microbe, e.g., a propionic acid producing microbe, e.g., *A. acidopropionici*, e.g., *A. acidopropionici* (NFS-2018), comprises about 5 to about 6.8, about 5 to about 6.6, about 5 to about 6.4, about 5 to about 6.2, about 5 to about 6, about 5 to about 5.8, about 5 to about 5.6, about 5 to about 5.4, about 5 to about 5.2, about 5.2 to about 7, about 5.2 to about 6.8, about 5.2 to about 6.6, about 5.2 to about 6.4, about 5.2 to about 6.2, about 5.2 to about 6, about 5.2 to about 5.8, about 5.2 to about 5.6, about 5.2 to about 5.4, about 5.4 to about 7, about 5.4 to about 6.8, about 5.4 to about 6.6, about 5.4 to about 6.4, about 5.4 to about 6.2, about 5.4 to about 6, about 5.4 to about 5.8, about 5.4 to about 5.6, about 5.6 to about 7, about 5.6 to about 6.8, about 5.6 to about 6.6, about 5.6 to about 6.4, about 5.6 to about 6.2, about 5.6 to about 6, about 5.6 to about 5.8, about 5.8 to about 7, about 5.8 to about 6.8, about 5.8 to about 6.6, about 5.8 to about 6.4, about 5.8 to about 6.2, about 5.8 to about 6, about 6 to about 7, about 6 to about 6.8, about 6 to about 6.6, about 6 to about 6.4, about 6 to about 6.2, about 6.2 to about 7, about 6.2 to about 6.8, about 6.2 to about 6.6, about 6.2 to about 6.4, about 6.4 to about 7, about 6.4 to about 6.8, about 6.4 to about 6.6, about 6.6 to about 7, about 6.6 to about 6.8, or about 6.8 to about 7 OD/ml (optical density) of an organic acid producing microbe, e.g., a propionic acid producing microbe, e.g., *A. acidopropionici*, e.g., *A. acidopropionici* (NFS-2018).

In some embodiments, the media is inoculated with about 1 to about 10% v/v of a culture of a lactic acid producing microbe, e.g., a lactic acid bacterium, e.g., *L. casei*. In some embodiments, the media is inoculated with about 1 to about 9, about 1 to about 8, about 1 to about 7, about 1 to about 6, about 1 to about 5, about 1 to about 4, about 1 to about 3, about 1 to about 2, about 2 to about 10, about 2 to about 9 about 2 to about 8, about 2 to about 7, about 2 to about 6, about 2 to about 5, about 2 to about 4, about 2 to about 3, about 3 to about 10, about 3 to about 9, about 3 to about 8, about 3 to about 7, about 3 to about 6, about 3 to about 5, about 3 to about 4, about 4 to about 10, about 4 to about 9, about 4 to about 8, about 4 to about 7, about 4 to about 6, about 4 to about 5, about 5 to about 10, about 5 to about 9, about 5 to about 8, about 5 to about 7, about 5 to about 6, about 6 to about 10, about 6 to about 9, about 6 to about 8, about 6 to about 7, about 7 to about 10, about 7 to about 9, about 7 to about 8, about 8 to about 10, about 8 to about 9, or about 9 to about 10% v/v of a lactic acid producing microbe, e.g., a lactic acid bacterium, e.g., *L. casei*.

In some embodiments, the culture of a lactic acid producing microbe, e.g., a lactic acid bacterium, e.g., *L. casei* comprises about 5 to about 7 OD/ml (optical density) of a lactic acid producing microbe, e.g., a lactic acid bacterium, e.g., *L. casei*. In some embodiments, the culture of a lactic acid producing microbe, e.g., a lactic acid bacterium, e.g., *L. casei*, comprises about 5 to about 6.8, about 5 to about 6.6, about 5 to about 6.4, about 5 to about 6.2, about 5 to about 6, about 5 to about 5.8, about 5 to about 5.6, about 5 to about 5.4, about 5 to about 5.2, about 5.2 to about 7, about 5.2 to about 6.8, about 5.2 to about 6.6, about 5.2 to about 6.4, about 5.2 to about 6.2, about 5.2 to about 6, about 5.2 to about 5.8, about 5.2 to about 5.6, about 5.2 to about 5.4, about 5.4 to about 7, about 5.4 to about 6.8, about 5.4 to about 6.6, about 5.4 to about 6.4, about 5.4 to about 6.2, about 5.4 to about 6, about 5.4 to about 5.8, about 5.4 to about 5.6, about 5.6 to about 7, about 5.6 to about 6.8, about 5.6 to about 6.6, about 5.6 to about 6.4, about 5.6 to about 6.2, about 5.6 to about 6, about 5.6 to about 5.8, about 5.8 to about 7, about 5.8 to about 6.8, about 5.8 to about 6.6, about 5.8 to about 6.4, about 5.8 to about 6.2, about 5.8 to about 6, about 6 to about 7, about 6 to about 6.8, about 6 to about 6.6, about 6 to about 6.4, about 6 to about 6.2, about 6.2 to about 7, about 6.2 to about 6.8, about 6.2 to about 6.6, about 6.2 to about 6.4, about 6.4 to about 7, about 6.4 to about 6.8, about 6.4 to about 6.6, about 6.6 to about 7, about 6.6 to about 6.8, or about 6.8 to about 7 OD/ml (optical density) of a lactic acid producing microbe, e.g., a lactic acid bacterium, e.g., *L. casei*.

In some embodiments, the lactic acid producing microbe, e.g., lactic acid bacterium, e.g., *L. casei* is inoculated into the medium at the same time as the organic acid producing microbe, e.g., a propionic acid producing microbe, e.g., *A. acidopropionici*, e.g., *A. acidopropionici* (NFS-2018). In some embodiments, the lactic acid producing microbe, e.g., lactic acid bacterium, e.g., *L. casei* is inoculated into the medium after the organic acid producing microbe, e.g., a propionic acid producing microbe, e.g., *A. acidopropionici*, e.g., *A. acidopropionici* (NFS-2018). In some embodiments, the lactic acid producing microbe, e.g., lactic acid bacterium, e.g., *L. casei* is inoculated into the medium about 6 to about 36 hours after the organic acid producing microbe, e.g., a propionic acid producing microbe, e.g., *A. acidopropionici*, e.g., *A. acidopropionici* (NFS-2018).

In some embodiments, the lactic acid producing microbe, e.g., lactic acid bacterium, e.g., *L. casei* is inoculated into the medium about 6 to about 36, about 6 to about 30, about 6 to about 24, about 6 to about 18, about 6 to about 12, about 12 to about 36, about 12 to about 30, about 12 to about 24, about 12 to about 18, about 18 to about 36, about 18 to about 30, about 18 to about 24, about 24 to about 36, about 24 to about 30, or about 30 to about 36 hours after the organic acid producing microbe, e.g., a propionic acid producing microbe, e.g., *A. acidopropionici*, e.g., *A. acidopropionici* (NFS-2018).

In some embodiments, the fermentation is carried out at about 30 to about 37° C. In some embodiments, the fermentation is carried out at about 30 to about 36, about 30 to about 35, about 30 to about 34, about 30 to about 33, about 30 to about 32, about 30 to about 31, about 31 to about 37, about 31 to about 36, about 31 to about 35, about 31 to about 34, about 31 to about 33, about 31 to about 32, about 32 to about 37, about 32 to about 36, about 32 to about 35, about 32 to about 34, about 32 to about 33, about 33 to about 37, about 33 to about 37, about 33 to about 36, about 33 to about 35, about 33 to about 34, about 34 to about 37, about 34 to about 36, about 34 to about 35, about 35 to about 37, about 35 to about 36, or about 36 to about 37° C.

In some embodiments, the fermentation is carried out in a volume of from about 1 to about 189,000 L. In some embodiments, the fermentation is carried out in a volume of from about 1 to about 180,000, about 1 to about 170,000, about 1 to about 160,000, about 1 to about 150,000, about 1 to about 140,000 about 1 to about 130,000, about 1 to about 120,000, about 1 to about 110,000, about 1 to about 100,000, about 1 to about 90,000, about 1 to about 80,000, about 1 to about 70,000, about 1 to about 60,000, about 1 to about 50,000, about 1 to about 40,000, about 1 to about 30,000, about 1 to about 20,000, about 1 to about 10,000, about 10,000 to about 189,000, about 10,000 to about 180,000, about 10,000 to about 170,000, about 10,000 to about 160,000, about 10,000 to about 150,000, about 10,000 to about 140,000, about 10,000 to about 130,000, about 10,000 to about 120,000, about 10,000 to about 110,000, about 10,000 to about 100,000, about 10,000 to about 90,000, about 10,000 to about 80,000, about 10,000 to about 70,000, about 10,000 to about 60,000, about 10,000 to about 50,000, about 10,000 to about 40,000 about 10,000 to about 30,000 about 10,000 to about 20,000, about 20,000 to about 189,000, about 20,000 to about 180,000, to about 20,000 to about 170,000, about 20,000 to about 160,000, about 20,000 to about 150,000, about 20,000 to about 140,000, about 20,000 to about 130,000, about 20,000 to about 120,000, about 20,000 to about 110,000, about 20,000 to about 100,000, about 20,000 to about 90,000 about 20,000 to about 80,000, about 20,000 to about 70,000, about 20,000 to about 60,000, about 20,000 to about 50,000, about 20,000 to about 40,000, about 20,000 to about 30,000, about 30,000 to about 189,000, about 30,000 to about 180,000, about 30,000 to about 170,000, about 30,000 to about 160,000, about 30,000 to about 150,000, about 30,000 to about 140,000, about 30,000 to about 130,000, about 30,000 to about 120,000, about 30,000 to about 110,000, about 30,000 to about 100,000, about 30,000 to about 90,000, about 30,000 to about 80,000, about 30,000 to about 70,000, about 30,000 to about 60,000, about 30,000 to about 50,000, about 30,000 to about 40,000, about 40,000 to about 189,000, about 40,000 to about 180,000, about 40,000 to about 170,000, about 40,000 to about 160,000, about 50,000 to about 160,000, about 50,000 to about 150,000, about 50,000 to about 140,000, about 50,000 to about 130,000, about 50,000 to about 120,000, about 50,000 to about 110,000, about 50,000 to about 100,000, about 50,000 to about 90,000, about 50,000 to about 80,000, about 50,000 to about 70,000, about 50,000 to about 60,000, about 60,000 to about 189,000, about 60,000 to about 180,000, about 60,000 to about 170,000, about 60,000 to about 160,000, about 60,000 to about 150,000, about 60,000 to about 140,000, about 60,000 to about 130,000, about 60,000 to about 120,000, about 60,000 to about 110,000, about 60,000 to about 100,000, about 60,000 to about 90,000, about 60,000 to about 80,000, about 60,000 to about 70,000, about 70,000 to about 189,000, about 70,000 to about 180,000, about 70,000 to about 170,000, about 70,000 to about 160,000, about 70,000 to about 150,000, about 70,000 to about 140,000, about 70,000 to about 130,000, about 70,000 to about 120,000, about 70,000 to about 110,000, about 70,000 to about 100,000, about 70,000 to about 90,000, about 70,000 to about 80,000, about 80,000 to about 189,000, about 80,000 to about 180,000, about 80,000 to about 170,000, about 80,000 to about 160,000, about 80,000 to about 150,000, about 80,000 to about 140,000, about 80,000 to about 130,000, about 80,000 to about 120,000, about 80,000 to about 110,000, about 80,000 to about 100,000, about 80,000 to about 90,000, about 90,000 to about 189,000, about 90,000 to about 180,000, about 90,000 to about 170,000, about 90,000 to about 160,000, about 90,000 to about 150,000, about 90,000 to about 140,000, about 90,000 to about 130,000, about 90,000 to about 120,000, about 90,000 to about 110,000, about 90,000 to about 100,000, about 100,000 to about 189,000, about 100,000 to about 180,000 about 100,000 to about 170,000, about 100,000 to about 160,000 about 100,000 to about 150,000, about 100,000 to about 140,000, about 100,000 to about 130,000, about 100,000 to about 120,000, about 100,000 to about 110,000, about 110,000 to about 189,000, about 110,000 to about 180,000, about 110,000 to about 170,000, about 110,000 to about 160,000, about 110,000 to about 150,000, about 110,000 to about 140,000, about 110,000 to about 130,000, about 110,000 to about 120,000, about 120,000 to about 189,000, about 120,000 to about 180,000, about 120,000 to about 170,000, about 120,000 to about 160,000, about 120,000 to about 150,000, about 120,000 to about 140,000, about 120,000 to about 130,000, about 130,000 to about 189,000, about 130,000 to about 180,000, about 130,000 to about 170,000, about 130,000 to about 160,000, about 130,000 to about 150,000, about 130,000 to about 140,000, about 140,000 to about 189,000, about 140,000 to about 180,000, about 140,000 to about 170,000, about 140,000 to about 160,000, about 140,000 to about 150,000, about 150,000 to about 189,000, about 150,000 to about 180,000, about 150,000 to about 170,000, about 150,000 to about 160,000, about 160,000 to about 189,000, about 160,000 to about 180,000, about 160,000 to about 170,000, about 170,000 to about 189,000, about 170,000 to about 180,000, or from about 180,000 to about 189,000 L.

The following table shows general parameters for media and culture that can be used in the present methods:

| | Exemplary parameters | Ranges |
| --- | --- | --- |
| Carbon Source (per L) | 72 g | 60-120 g/L |
| Nitrogen source | 2% yeast extract | 1-2.5% |
| Vitamins (per L) | (vitamin B12) 0.002 g | 0.0015-0.004 g |
| Magnesium sulfate (per L) | 0.4 g | 0.2-0.8 g |
| Sodium diphosphate (per L) | 3 g | 1.5-5 g |
| Potassium diphosphate (per L) | 1 g | 0.5-3 g |
| Inoculum volume (% v/v) | 5% | 1-10% |
| pH | 6.0 | 5.5-7, or 5.5-6.9 |
| Temperature | 30 | 30-37 |
| Fermentation run time (hrs) | 168 | 144-196 |
| Pressure (bars) | Ambient pressure | 0.5-1 |
| Flocculation (rpm) | 200 | 150-300 |

Fermentation Approaches

A number of different fermentation approaches are known in the art and can be used in the methods described herein.

In some embodiments, the fermentation is a batch, fed-batch, sequential batch, repeated batch, or continuous batch fermentation.

In some embodiments, the fermentation is carried out in a bioreactor. In some embodiments, the bioreactor is a PEI-Poraver bioreactor. In some embodiments, the bioreactor is a fibrous-bed bioreactor. In some embodiments, the fibrous-bed bioreactor is a multi-point fibrous-bed bioreactor. In some embodiments, the fibrous-bed bioreactor is a plant fibrous-bed bioreactor.

In some embodiments, the fermentation is immobilized cell fermentation.

In some embodiments, the fermentation is supplemented with additional media and/or media components during the course of the reaction.

In some embodiments, the media is supplemented with one or more of a carbon sources, a nitrogen source, a vitamin source, magnesium sulfate, or sodium diphosphate, e.g., as described herein.

Processing

The methods described herein may include processing and/or refinement of the organic acid(s), e.g., propionic acid, produced during the fermentations described herein. In some embodiments, the fermentation is terminated, and the organic acid(s) are extracted from the culture. In some embodiments, part of the culture is removed for processing before the fermentation is terminated. In some embodiments, fermentation is terminated within the part of the culture removed for processing.

In some embodiments, the fermentation is terminated through heat-killing. In some embodiments, the fermentation is terminated by separating cells from the culture medium, e.g., by filtration or other physical means.

15

Examples

Methods

Growth medium was sterilized at 121° C. for 1 hour, and then allowed to cool to 30° C. Vitamin B12 was added post sterilization and headspace was replaced with nitrogen gas for 2 hrs when using 3 L bioreactors and sparged nitrogen gas for 48 hrs when using 30 L fermenter. The 48 hr pre-grown propionic acid bacteria was inoculated into the fermented sugar medium at 0 hrs. If used, the lactic acid bacteria was added to the fermenter after 12-24 hrs. The fermentation is carried out for 168 hrs then the cells are heat killed for 1 hr for further downstream processing. This process was also used for mono-culture fermentation of NFS-2018 without the addition of lactic acid bacteria.

Example 1. PA Production of *A. Acidopropionici* (NFS-2018)—30 L Reaction

*A. acidopropionici* (NFS-2018) was cultivated from a frozen glycerol stock at 30° C. under anaerobic condition in M24 medium supplemented with 2% glucose. The cells were sub-cultured every 48 hrs into fresh M24 medium starting at 10 mL then into 50 ml (2-30 DS/ml) to use as seeds for the 1 L bioreactor vessels.

Fermentation was performed at 30 L working volume in a 42 L fermenter. The following was added to the fermenter containing 25 L of ddH$_2$O while stirring: 1.8 kg of dextrose (6%), 250 g (1%) of yeast extract+20 g MgSO$_4$ (0.08%), 0.15 g of MnSO$_4$ (0.0015%), 75 g NaPO$_4$ (dibasic: 0.3%), and 25 g KPO$_4$ (dibasic: 0.1%) into the fermenter while stirring. Mix thoroughly then autoclave for 1 hr at 121° C. The temperature was lowered to 30° C. and the pH was lowered to 6 using with 15M NaOH. Vitamin B12 solution was added to the fermenter at a final concentration of 2 mg/L. The fermenter was inoculated with 1.5 L (5-7 ODs) of 48 hr pre-grown *A. acidopropionici* (NFS-2018). Samples were removed every 12-24 hrs for glucose and organic acid analysis using a YSI analyzer and HPLC respectively. 2-3% glucose was added accordingly throughout the fermentation run. After 168 hrs, the fermentation was terminated by heat kill for 1 hr at 80° C. The broth was harvested for further downstream processing.

The results showed that when NFS-2018 was cultivated by itself in the fermenter the maximum PA reached was 53 g/L at 168 hrs. See Table 1.

Example 2. PA Production of *A. Acidopropionici* (NFS-2018) when Using Co-Culture with *L. casei*—1 L Reaction

*A. acidopropionici* (NFS-2018) and *Lactobacillus casei* were cultivated from frozen glycerol stocks at 30° C. under anaerobic condition in M24 medium supplemented with 2% glucose. The cells were sub-cultured every 48 hrs into fresh M24 medium starting at 10 mL then into 50 ml (2-30 DS/ml) to use as seeds for the 1 L bioreactor vessels Fermentation was performed at 1 L volume in a 3 L fermenter. The following was added to the fermenter containing 1 L of ddH$_2$O while stirring: 70 g of dextrose, 10 g (1%) of yeast extract+0.4 g MgSO$_4$(0.08%), 3 g NaPO$_4$ (dibasic: 0.3%), and 1 g KPO$_4$ (dibasic: 0.1%). Mix thoroughly then autoclave for 1 hr at 121° C. The temperature was lowered to 30° C. and the pH was lowered to 6 using 15M NaOH. Vitamin B12 solution was added to the fermenter at a final concentration of 2 mg/L. The fermenter was inoculated with 1.5 L (5-7 ODs) of 48 hr pre-grown *A. acidopropionici* (NFS-2018) at 0 hr. 1.5 L of *L. casei* (5-7 ODs/ml) was added to the bioreactor at the 24 hrs point of the fermentation. Samples were removed every 12-24 hrs for glucose and organic acid analysis using a YSI analyzer and HPLC respectively. 2-3% of glucose and another 1% of yeast extract was added accordingly throughout the fermentation run. After 168 hrs, the fermentation was terminated by heat kill for 1 hr at 80° C. The broth was harvested for further downstream processing.

The results showed that when NFS-2018 and *Lactobacillus casei* was conducted as a co-culture in the bioreactor the maximum PA reached was 68 g/L at 168 hrs. See Table 1.

Example 3. PA Production of *A. Acidopropionici* (NFS-2018) when Using Co-Culture with *L. casei*—30 L Reaction

*A. acidopropionici* (NFS-2018) and *Lactobacillus casei* were cultivated from frozen glycerol stocks at 30° C. under anaerobic condition in M24 medium supplemented with 2% glucose. The cells were sub-cultured every 48 hrs into fresh M24 medium starting at 10 mL then into 50 ml (2-3 ODs/ml) to use as seeds for the 1 L bioreactor vessels.

Fermentation were performed at 30 L volume in a 42 L fermenter. The following was added to the fermenter containing 25 L of ddH$_2$O while stirring: 1.8 kg of dextrose (6%), 250 g (1%) of yeast extract+20 g MgSO$_4$(0.08%), 0.15 g of MnSO$_4$(0.0015%), 75 g NaPO$_4$ (dibasic: 0.3%), and 25 g KPO$_4$(dibasic: 0.1%) into the fermenter while stirring. Mix thoroughly then autoclave for 1 hr at 121°. The temperature was lowered to 30° C. and the pH was lowered to 6.0 using 15M NaOH. Vitamin B12 solution was added to the fermenter at a final concentration of 2 mg/L. The fermenter was inoculated with 1.5 L (5-7 ODs) of 48 hr pre-grown *A. acidopropionici* (NFS-2018) at 0 hrs. A 1.5 L (5-7 ODs) of 48 hr pre-grown *L. casei* was added after 12 hrs. Samples were removed every 12-24 hrs for glucose and organic acid analysis using a YSI analyzer and HPLC respectively. 2-3% glucose was added accordingly throughout the fermentation run. After 168 hrs, the fermentation was terminated by heat kill for 1 hr at 80° C. The broth was harvested for further downstream processing.

The results showed that when NFS-2018 and *Lactobacillus casei* was conducted as a co-culture in the bioreactor the maximum PA reached was 63 g/L at 168 hrs. See Table 1.

TABLE 1

| | | | Propionic acid | Acetic Acid | Lactic acid | Succinic acid |
|---|---|---|---|---|---|---|
| Fermentation runs | Single or co-culture | Volume (L) | (g/L) | (g/L) | (g/L) | (g/L) |
| Ntk-071 | Single | 30 | 53.5 | 9.5 | BLD | 16.4 |
| Ntk-084 | co-culture | 1 | 68.5 | 9.5 | BLD | 10.8 |
| Ntk-086 | co-culture | 30 | 63.1 | 6.3 | BLD | 8.8 |

FERMENTATION: NFS-2018 VS. NFS-2018 + *LACTOBACILLUS CASEI*

REFERENCES

1. Wang Z, Jin Y, Yang ST. 2015. High cell density propionic acid fermentation with an acid tolerant strain of *Propionibacterium acidipropionici*. Biotechnol Bioeng 112: 502-511.
2. Liu Y, Zhang Y G, Zhang R B, Zhang F, Zhu J. 2011. Glycerol/glucose co-fermentation: one more proficient process to produce propionic acid by *Propionibacterium acidipropionici*. Curr Microbiol 62:152-158.

3. Wang Z, Ammar E M, Zhang A, Wang L, Lin M, Yang ST. 2015. Engineering *Propionibacterium freudenreichii* subsp. *shermanii* for enhanced propionic acid fermentation: effects of overexpressing propionyl-CoA:Succinate CoA transferase. Metab Eng 27:46-56.

4. Jiang L, Cui H, Zhu L, Hu Y, Xu X, Li S, Huang H. 2015. Enhanced propionic acid production from whey lactose with immobilized *Propionibacterium acidipropionici* and the role of trehalose synthesis in acid tolerance. Green Chemistry 17:250-259.

5. Border P M, Kierstan M P J, Plastow GS. 1987. Production of propionic acid by mixed bacterial fermentation. Biotechnology Letters 9:843-848.

6. Zhang A, Yang S-T. 2009. Propionic acid production from glycerol by metabolically engineered *Propionibacterium acidipropionici*. Process Biochemistry 44:1346-1351.

7. Wang Z, Yang S-T. 2013. Propionic acid production in glycerol/glucose co-fermentation by *Propionibacterium freudenreichii* subsp. *shermanii*. Bioresource Technology 137:116-123.

8. Stowers C C, Cox B M, Rodriguez B A. 2014. Development of an industrializable fermentation process for propionic acid production. Journal of Industrial Microbiology & Biotechnology 41:837-852.

9. Gonzalez-Garcia R A, McCubbin T, Navone L, Stowers C, Nielsen L K, Marcellin E. 2017. Microbial Propionic Acid Production. Fermentation 3:21.

10. Kagliwal L D, Survase S A, Singhal R S, Granstrom T. 2013. Wheat flour based propionic acid fermentation: An economic approach. Bioresource Technology 129:694-699.

11. Ahmadi N, Khosravi-Darani K, Mortazavian A M. 2017. An overview of biotechnological production of propionic acid: From upstream to downstream processes. Electronic Journal of Biotechnology 28:67-75.

12. Woskow S. A., B. A. Glatz. 1991. Propionic acid production by a propionic acid-tolerant strain of *Propionibacterium acidipropionici* in batch and semicontinuous fermentation. Applied and Environmental Microbiology 57:2821-2828.

13. Zhu Y., J. Li, M. Tan, L. Liu, L. Jiang, J. Sun, P. Lee, G. Du, J. Chen. 2010. Optimization and scale-up of propionic acid production by propionic acid-tolerant *Propionibacterium acidipropionici* with glycerol as the carbon source. Bioresource Technology 101:8902-8906.

14. Zhuge X., L. Liu, H.-d. Shin, J. Li, G. Du, J. Chen. 2014. Improved propionic acid production from glycerol with metabolically engineered *Propionibacterium jensenii* by integrating fed-batch culture with a pH-shift control strategy. Bioresource Technology 152:519-525.

15. Zhuge X., J. Li, H.-d. Shin, L. Liu, G. Du, J. Chen. 2015. Improved propionic acid production with metabolically engineered *Propionibacterium jensenii* by an oxidoreduction potential-shift control strategy. Bioresource Technology 175:606-612.

16. Coral J. 2008. Propionic acid production by *Propionibacterium* sp. using low-cost carbon sources in submerged fermentation. Dissertation. Federal University of Parana.

17. Zhang A., J. Sun, Z. Wang, S.-T. Yang, H. Zhou. 2015. Effects of carbon dioxide on cell growth and propionic acid production from glycerol and glucose by *Propionibacterium acidipropionici*. Bioresource Technology 175:374-381.

18. Wang Z., M. Lin, L. Wang, E. M. Ammar, S.-T. Yang. 2015. Metabolic engineering of *Propionibacterium freudenreichii* subsp. *shermanii* for enhanced propionic acid fermentation: Effects of overexpressing three biotin-dependent carboxylases. Process Biochemistry 50:194-204.

19. Suwannakham S., Y. Huang, S.-T. Yang. 2006. Construction and characterization of ack knock-out mutants of *Propionibacterium acidipropionici* for enhanced propionic acid fermentation. Biotechnology and Bioengineering 94:383-95.

20. Suwannakham S., S.-T. Yang. 2005. Enhanced propionic acid fermentation by *Propionibacterium acidipropionici* mutant obtained by adaptation in a fibrous-bed bioreactor. Biotechnology and Bioengineering 91:325-337.

21. Suwannakham S. 2005. Metabolic engineering for enhanced propionic acid fermentation by *Propionibacterium acidipropionici*. Dissertation. Ohio State University.

22. Tufvesson P., A. Ekman, R. R. R. Sardari, K. Engdahl, L. Tufvesson. 2013. Economic and environmental assessment of propionic acid production by fermentation using different renewable raw materials. Bioresource Technology 149:556-564.

23. Thierry A., S.-M. Deutsch, H. Falentin, M. Dalmasso, F. J. Cousin, G. January 2011. New insights into physiology and metabolism of *Propionibacterium freudenreichii*. International Journal of Food Microbiology 149:19-27.

24. Scholz C. F. P., M. Kilian. 2016. The natural history of cutaneous propionibacteria, and reclassification of selected species within the genus *Propionibacterium* to the proposed novel genera *Acidipropionibacterium* gen. nov., Cutibacterium gen. nov. and *Pseudopropionibacterium* gen. nov. International Journal of Systematic and Evolutionary Microbiology 66:4422-4432.

25. Rehberger J. L., B. A. Glatz. 1998. Response of cultures of *Propionibacterium* to acid and low pH: tolerance and inhibition. Journal of Food Production 61:211-216.

26. Guan N., L. Liu, X. Zhug, Q. Xu, J. Li, G. Du, J. Chen. 2012. Genome-shuffling improves acid tolerance of *Propionibacterium acidipropionici* and propionic acid production. Advances in Chemistry Research 15:143-152.

27. Guan N., H. Shin, R. R. Chen, J. Li, L. Liu, G. Du, J. Chen. 2014. Understanding of how *Propionibacterium acidipropionici* respond to propionic acid stress at the level of proteomics. Scientific Reports 4:6951.

28. Guan N., H. D. Shin, G. Du, J. Chen, L. Liu. 2016. Metabolic engineering of acid resistance elements to improve acid resistance and propionic acid production of *Propionibacterium jensenii*. Biotechnology and Bioengineering 113:1294-304.

29. EP 0141642
30. WO 85/04901
31. US 2011/0151529 A1
32. WO 2012/064883 A2
33. WO 2017/055932 A2

What is claimed is:

1. A method for producing propionic acid, the method comprising:

providing acid-tolerant propionic acid excreting microbes selected from the group consisting of *Propionibacterium, Anaerovibrio, Bacteroides, Clostridium, Fusobacterium, Megasphaera, Propionispira, Selenomonas, Veillonella*, and combinations thereof;

providing acid-tolerant lactic acid producing microbes selected from the group consisting of *Lactococcus, Pediococcus, Oenococus, Enterococcus, Leuconostoc,*

*Bifidobacterium, Bacillus, Lactobacillus, Clostridium, Paenibacillus*, Sporolactobacillus, and combinations thereof;

providing a growth medium comprising a glucose carbon source and a lactose carbon source, and having a pH of between 5.8 and 6.5;

adding the acid-tolerant propionic acid excreting microbes and the acid-tolerant lactic acid producing microbes to the growth medium, wherein the acid-tolerant lactic acid producing microbes are added to the growth medium 6-36 hours after the acid-tolerant propionic acid excreting microbes are added to the growth medium, thereby producing a co-culture;

incubating the co-culture in fermentation, thereby producing propionic acid; and maintaining the co-culture for a time sufficient to produce a desired amount of propionic acid.

2. The method of claim 1, wherein the *Propionibacterium* genus microbes are *Acidipropionibacterium acidipropionici* (NF S-2018).

3. The method of claim 1, wherein the acid-tolerant propionic acid excreting microbes are provided as a growing culture.

4. The method of claim 1, wherein the acid-tolerant lactic acid producing microbes are selected from the group consisting of *Lactococcus, Pediococcus, Oenococus, Enterococcus, Leuconostoc, Bifidobacterium*, and *Bacillus*.

5. The method of claim 4, wherein the acid-tolerant lactic acid producing microbes are provided as a growing culture.

6. The method of claim 1, wherein the acid-tolerant lactic acid producing microbes are selected from the group consisting of *Bacillus, Lactobacillus, Clostridium, Paenibacillus, Sporolactobacillus*, and combinations thereof.

7. The method of claim 6, wherein the acid-tolerant lactic acid producing microbes are *Lactobacillus casei*.

8. The method of claim 6, wherein the acid-tolerant lactic acid producing microbes are provided as spores.

9. The method of claim 8, wherein the spores are provided as part of the carbon source.

10. The method of claim 1, wherein the pH of the growth medium is 6.0.

11. The method of claim 1, wherein the growth medium further comprises a nitrogen source, vitamins, $MgSO_4$, $NaPO_4$, and $KPO_4$.

12. The method of claim 11, wherein the nitrogen source is selected from yeast extract, peptides, ammonia sulfate, ammonia hydroxide, amino acids, and combinations thereof.

13. The method of claim 12, wherein the nitrogen source is yeast extract.

14. The method of claim 11, wherein the vitamin is vitamin B12.

15. The method of claim 1, wherein the glucose carbon source and the lactose carbon source are the same.

16. The method of claim 1, wherein the glucose carbon source and the lactose carbon source are different.

17. The method of claim 1, wherein the glucose carbon source is a plant-based glucose carbon source.

18. The method of claim 17, wherein the plant-based glucose carbon source is selected from the group consisting of hydrolyzed wheat, hydrolyzed corn, hydrolyzed beans, hydrolyzed starch, and combinations thereof.

19. The method of claim 1, wherein the lactose carbon source is whey.

20. The method of claim 1, wherein the acid-tolerant lactic acid producing microbes are added to the growth medium 12-24 hours after the acid-tolerant propionic acid excreting microbes are added to the growth medium;

and maintaining the co-culture for a time sufficient to produce a desired amount of propionic acid.

\* \* \* \* \*